(12) United States Patent
Oeser et al.

(10) Patent No.: US 10,334,854 B2
(45) Date of Patent: Jul. 2, 2019

(54) HERBICIDE COMBINATIONS COMPRISING GLUFOSINATE AND INDAZIFLAM

(71) Applicant: BAYER CROPSCIENCE AKTIENGESELLSCHAFT, Monheim am Rhein (DE)

(72) Inventors: Jörg Oeser, Mülheim an der Ruhr (DE); Petra Gür, Seligenstadt (DE); Michael Schwarz, Raleigh, NC (US)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/568,081

(22) PCT Filed: Apr. 25, 2016

(86) PCT No.: PCT/EP2016/059132
§ 371 (c)(1),
(2) Date: Oct. 20, 2017

(87) PCT Pub. No.: WO2016/173966
PCT Pub. Date: Nov. 3, 2016

(65) Prior Publication Data
US 2018/0110230 A1     Apr. 26, 2018

Related U.S. Application Data

(60) Provisional application No. 62/293,489, filed on Feb. 10, 2016.

(51) Int. Cl.
*A01N 57/20* (2006.01)
*A01N 43/66* (2006.01)
*A01N 43/68* (2006.01)

(52) U.S. Cl.
CPC .......... *A01N 57/20* (2013.01); *A01N 43/66* (2013.01); *A01N 43/68* (2013.01)

(58) Field of Classification Search
None
See application file for complete search history.

(56) References Cited

U.S. PATENT DOCUMENTS

| | | | |
|---|---|---|---|
| 4,168,963 A | 9/1979 | Rupp et al. | |
| 4,521,348 A | 6/1985 | Finke et al. | |
| 4,599,207 A | 7/1986 | Lachhein et al. | |
| 5,258,358 A | 11/1993 | Kocur et al. | |
| 5,491,125 A | 2/1996 | Albrecht et al. | |
| 6,069,114 A | 5/2000 | Lorenz et al. | |
| 6,359,162 B1 | 3/2002 | Willms et al. | |
| 2005/0266995 A1 | 12/2005 | Frisch et al. | |
| 2005/0266998 A1 | 12/2005 | Frisch et al. | |
| 2005/0266999 A1 | 12/2005 | Frisch et al. | |
| 2006/0014642 A1 | 1/2006 | Hacker et al. | |
| 2007/0184982 A1 | 8/2007 | Long | |
| 2008/0045415 A1 | 2/2008 | Baur et al. | |

FOREIGN PATENT DOCUMENTS

| | | |
|---|---|---|
| CN | 103329931 | * 10/2013 |
| CN | 103329931 A | 10/2013 |
| EP | 0048436 A1 | 3/1982 |
| EP | 0336151 A2 | 10/1989 |
| EP | 2147600 A1 | 1/2010 |
| WO | 00/16627 A1 | 3/2000 |
| WO | 2004/069814 A1 | 8/2004 |
| WO | 2006/007947 A1 | 1/2006 |
| WO | 2010/009819 A2 | 1/2010 |

OTHER PUBLICATIONS

Jhala et al.(Tank mixing Saflufenacil, Glufosinate, and Indaziflam Improved Burndown and Residual Weed Control, Weed Technology, 2013, 27: 422-429) (Year: 2013).*

Perez'-Lo'pez et al.(Characterization of Glyphosate-Resistant Tropical Sprangletop(*Leptochloa virgate*) and Its Alternative Chemical Control in Persian Lime Orchards in Mexico, Weed Technology, 2014, 62: 441-450) (Year: 2014).*

Jhala, Amit J. et al., "Tank Mixing Saflufenacil, Glufosinate, and Indaziflam Improved Burndown and Residual Weed Control," Weed Technology, vol. 27, No. 2, Jan. 1, 2013, pp. 422-429, XP009183223.

Web Downloads: URL: http://horticulture.oregonstate.edu/system/files/u225/2012CombinedHortWeedControlReport.pdf, "Horticultural Weed Control Report 2012," Jan. 1, 2012 [Retrieved Jul. 8, 2015], pp. 30-32.

\* cited by examiner

*Primary Examiner* — Alton N Pryor
(74) *Attorney, Agent, or Firm* — McBee Moore Woodward & Vanik IP, LLC

(57) ABSTRACT

The present invention primarily relates to specific herbicide combinations comprising (i) glufosinate and/or salts thereof and (ii) indaziflam and to compositions comprising said specific herbicide combinations. The present invention further relates to a method of producing said specific herbicide combinations and compositions comprising said specific herbicide combinations. The present invention also relates to the use of said specific herbicide combinations and compositions comprising said specific herbicide combinations in the field of agriculture, in particular as plant growth regulators and for controlling harmful plants or undesired plant growth, as well as to corresponding methods.

18 Claims, No Drawings

HERBICIDE COMBINATIONS COMPRISING GLUFOSINATE AND INDAZIFLAM

CROSS REFERENCE TO RELATED APPLICATIONS

This application is a National Stage entry of International Application No. PCT/EP2016/059132 filed 25 Apr. 2016, which claims priority to U.S. Application No. 62/293,489, filed 10 Feb. 2016 and which claims priority to European Patent Application No. 15165281.5, filed 27 Apr. 2015.

BACKGROUND

Field

The present invention primarily relates to specific herbicide combinations comprising (i) glufosinate and/or salts thereof and (ii) indaziflam and to compositions comprising said specific herbicide combinations. The present invention further relates to a method of producing said specific herbicide combinations and compositions comprising said specific herbicide combinations. The present invention also relates to the use of said specific herbicide combinations and compositions comprising said specific herbicide combinations in the field of agriculture, in particular as plant growth regulators and for controlling harmful plants or undesired plant growth, as well as to corresponding methods.

Description of Related Art

U.S. Pat. No. 4,168,963 describes phosphorus-containing compounds with herbicidal activity, of which, in particular, phosphinothricin (2-amino-4-[hydroxy(methyl)phosphinoyl]butanoic acid; common name: glufosinate) and its salts have acquired commercial importance in the agrochemistry (agricultural chemistry) sector.

WO 00/16627 A1 teaches synergistic active substance combinations for controlling harmful plants, wherein as active substance (A) amino triazines of a certain structure type are used.

WO 2004/069814 A1 describes amino-1,3,5 triazines N-substituted with chiral bicyclic radicals, and their use as herbicides and plant growth regulators.

WO 2006/007947 A1 discloses various herbicide combinations, comprising constituents (A) and (B), wherein as one possible constituent (A) indaziflam is mentioned, and as constituent (B) a large number of many differend other herbicides are listed.

WO 2010/009819 A2 relates to a method for selective weed control in turf or lawn by using compounds of formula (I) defined therein. In WO 2010/009819 A2, indaziflam is one of the compounds of formula (I), and also certain combinations of the compounds of formula (I) with further herbicides are disclosed in WO 2010/009819 A2.

Weed Technology 2013, 27, 422-429 reports on the burndown and weed control to protect citrus plants by tank mixing saflufenacil, glufosinate and indaziflam.

CN 103 329 931 describes compositions of indaziflam and glufosinate in a ratio of 1:(0.2 to 10).

The Horticultural Weed Control Report 2012 from the Oregon State University describes inter alia weed control in hazelnuts in Lane County, Oreg., where also mixtures of glufosinate and indaziflam were used.

In their application, herbicidal crop protection agents (herbicides) known to date for controlling harmful plants or unwanted vegetation, e.g. in permanent crops or on permanent cropland, have some disadvantages, be it (a) that they have no or else insufficient herbicidal activity against specific harmful plants, (b) that the spectrum of harmful plants which can be controlled with the herbicides is not broad enough, (c) that the selectivity of herbicides in and the compatibility with (young) plantation crops is too low, thereby causing unwanted damage and/or unwanted reduced harvest yields of the (young) plantation crops, (d) that the initial herbicidal activity is not high or not strong enough and/or (e) that the herbicidal activity does not last long enough.

Overall, the herbicidal activity, i.e. one or more of the above aspects (a), (b) (c), (d) and/or (e) of the herbicides like glufosinate and/or agronomically acceptable salts thereof used so far still allow some improvement.

SUMMARY

Surprisingly, it has now been found that certain herbicide combinations or compositions comprising said herbicide combinations exhibit the desired herbicidal activity and are able to control harmful plants or unwanted vegetation in a more effective and more efficient manner.

The present invention primarily relates to a combination of herbicides (herbicide combination) comprising or consisting of
(i) glufosinate and/or agronomically acceptable salts thereof, and
(ii) indaziflam,
wherein the ratio by weight of the total amount of component (i) to the total amount of component (ii) ≥25:1, i.e. said ratio by weight is equal to or greater than 25:1.

DETAILED DESCRIPTION OF A PREFERRED EMBODIMENT

Preferably, the ratio by weight of the total amount of component (i) to the total amount of component (ii) in a herbicide combination according to the present invention is in the range of from 25:1 to 50:1.

Preferably, in a herbicide combination according to the present invention the ratio by weight of the total amount of component (i) to the total amount of component (ii) is ≥26:1, i.e. said ratio by weight preferably is equal to or greater than 26:1, more preferably ≥27:1, i.e. said ratio by weight is more preferably equal to or greater than 27:1.

Preferably, the ratio by weight of the total amount of component (i) to the total amount of component (ii) in a herbicide combination according to the present invention is in the range of from 26:1 to 50:1, more preferably in the range of from 27:1 to 50:1.

More preferably, the ratio by weight of the total amount of component (i) to the total amount of component (ii) in a herbicide combination according to the present invention is in the range of from 30:1 to 50:1, even more preferably in the range of from 30:1 to 40:1.

Further, the present invention also relates to a composition comprising a herbicide combination as defined hereinabove or hereinafter.

Thus, a composition according to the present invention comprises
(i) glufosinate and/or agronomically acceptable salts thereof, and
(ii) indaziflam,
wherein the ratio by weight of the total amount of component (i) to the total amount of component (ii) in said composition is ≥25:1, i.e. said ratio by weight is equal to or greater than 25:1, based on the total weight of the composition.

Preferably, the ratio by weight of the total amount of component (i) to the total amount of component (ii) in a composition according to the present invention is in the range of from 25:1 to 50:1, based on the total weight of the composition.

Preferably, in a composition according to the present invention the ratio by weight of the total amount of component (i) to the total amount of component (ii) is ≥26:1, i.e. said ratio by weight preferably is equal to or greater than 26:1, more preferably ≥27:1, i.e. said ratio by weight is more preferably equal to or greater than 27:1, based on the total weight of the composition.

Preferably, the ratio by weight of the total amount of component (i) to the total amount of component (ii) in a composition according to the present invention is in the range of from 26:1 to 50:1, more preferably in the range of from 27:1 to 50:1, based on the total weight of the composition.

More preferably, the ratio by weight of the total amount of component (i) to the total amount of component (ii) in a composition according to the present invention is in the range of from 30:1 to 50:1, even more preferably in the range of from 30:1 to 40:1, based on the total weight of the composition.

The herbicide combinations and the compositions comprising said herbicide combinations in accordance with the present invention exhibit an excellent herbicidal activity in controlling harmful plants or unwanted vegetation.

It has been found that the efficacy of glufosinate and/or agronomically acceptable salts thereof can be improved by combining glufosinate and/or agronomically acceptable salts thereof with indaziflam in the ratio by weight as specified in the context of the present invention.

The (use of a) herbicide combination according to the present invention and the (use of a) composition comprising the herbicide combination as defined in the context of the present invention show remarkably higher/stronger initial herbicidal activity (see above mentioned aspect (d)) than glufosinate and/or agronomically acceptable salts thereof alone.

The (use of a) herbicide combination according to the present invention and the (use of a) composition comprising the herbicide combination as defined in the context of the present invention show remarkably longer lasting herbicidal activity (see above mentioned aspect (e)) than glufosinate and/or agronomically acceptable salts thereof alone. For example, said longer lasting herbicidal activity results in the substantial retardation or substantial suppression of regrowth of the harmful or undesired plants and/or substantial retardation or substantial suppression of germination of the harmful or undesired plants (see also the biological examples below).

The (use of a) herbicide combination according to the present invention and the (use of a) composition comprising the herbicide combination as defined in the context of the present invention is characterized by an overall more rapidly commencing (i.e. earlier and faster) and a more long-lasting herbicidal action, in comparison to glufosinate and/or agronomically acceptable salts thereof alone, when applied to harmful or undesired plants, parts of said harmful or undesired plants, or the area where the harmful or undesired plants grow, for example the area under cultivation, especially in post-emergence application.

Thus, indaziflam (component (ii) as defined in the context of the present invention) enhances, extends, and/or prolongs the herbicidal activity of glufosinate and/or agronomically acceptable salts thereof (component (i) as defined in the context of the present invention).

The (use of a) herbicide combination according to the present invention and the (use of a) composition comprising the herbicide combination as defined in the context of the present invention also allow good selectivity in and the compatibility with (young) plantation crops (see above mentioned aspect (c)), thereby avoiding or reducing unwanted damage and/or unwanted reduced harvest yields of the (young) plantation crops.

If a herbicide combination (used) according to the present invention or if a composition comprising the herbicide combination (used) in the context of the present invention is applied to the green parts of the harmful plants or undesired plants, growth likewise stops drastically a very short time after the treatment; typically, they die completely after a certain time, so that in this manner competition by the weeds, which is harmful to the (permanent) crops, is eliminated at a very early point in time and in a sustained manner.

In addition, the (use of a) herbicide combination according to the present invention and the (use of a) composition comprising the herbicide combination as defined in the context of the present invention allow very effective and efficient tree sucker control, and exhibit good and improved rainfastness.

Further, the herbicide combinations (used) in accordance with the present invention and the compositions comprising said herbicide combinations (used) in accordance with the present invention can be employed as plant growth regulators.

The present invention further relates to a composition as defined herein in the context of the present invention which additionally comprises one or more further components selected from the group consisting of formulation auxiliaries, additives customary in crop protection, and further agrochemically active compounds (i.e. agrochemically active compounds different from components (i) and (ii) as defined above, i.e. agrochemically active compounds other than (i) glufosinate and/or agronomically acceptable salts thereof and (ii) indaziflam).

In a preferred embodiment, a combination of herbicides used in the context of the present invention and a composition as defined herein in the context of the present invention is free of saflufenacil.

However, when a combination of herbicides used in the context of the present invention consists of herbicides (i) glufosinate and/or agronomically acceptable salts thereof and (ii) indaziflam, this means that in such a case the combination of herbicides used in the context of the present invention or the composition comprising said combination of herbicides used in the context of the present invention does not contain any further (i.e. no additional) herbicidal active ingredient, and preferably does not contain any further agrochemically active compound. Such combinations of herbicides consisting of (i) glufosinate and/or agronomically acceptable salts thereof (glufosinate-ammonium being preferred) and (ii) indaziflam are particularly preferred in the context of the present invention.

In this context, the term "further herbicidal active ingredient" and "further agrochemically active compound" refers to the herbicides and agrochemically active compounds (pesticides), respectively, listed in "The Pesticide Manual", 16th edition, The British Crop Protection Council and the Royal Soc. of Chemistry, 2012 other than glufosinate and/or agronomically acceptable salts thereof, and indaziflam.

In a preferred composition according to the present invention, the total amount of component (i) is equal to or less than 600 g/L (g/L=gram per liter), more preferably the total amount of component (i) is equal to or less than 450 g/L, and even more preferably the total amount of component (i) is equal to or less than 300 g/L, in each case based on the total amount of the composition.

Preferably, the total amount of component (i) in a composition according to the present invention in the range of from 100 to 600 g/L, preferably in the range of from 125 to 450 g/L, more preferably in the range of from 125 to 300 g/L, even preferably in the range of from 125 to 250 g/L, in each case based on the total amount of the composition.

In a preferred composition according to the present invention, the total amount of component (ii) is in the range of from 2 to 20 g/L, preferably in the range of from 3 to 15 g/L, more preferably in the range of from 3 to 12 g/L, even preferably in the range of from 3 to 10 g/L, most preferably in the range of from 3 to 6 g/L, in each case based on the total amount of the composition.

Preferably, a composition according to the present invention is a composition, wherein
the total amount of component (i) is in the range of from 125 to 300 g/L, preferably in the range of from 125 to 250 g/L, and
the total amount of component (ii) is in the range of from 3 to 10 g/L, preferably in the range of from 3 to 6 g/L,
in each case based on the total amount of the composition.

Thus, preferably, a composition according to the present invention is a composition, wherein
the total amount of component (i) is in the range of from 125 to 300 g/L,
and
the total amount of component (ii) is in the range of from 3 to 10 g/L,
in each case based on the total amount of the composition.

Also, preferably, a composition according to the present invention is a composition, wherein
the total amount of component (i) is in the range of from 125 to 250 g/L,
and
the total amount of component (ii) is in the range of from 3 to 10 g/L,
in each case based on the total amount of the composition.

Own experiments have shown that compositions according to the present invention comprising a total amount of component (i) in the range of from 200 to 250 g/L, and a total amount of component (ii) in the range of from 6 to 10 g/L, in each case based on the total amount of the composition, are particularly suitable in the context of the present invention.

For example, a composition according to the present invention comprising a total amount of component (i) of about 250 g/L, and a total amount of component (ii) of about 7.5 g/L, in each case based on the total amount of the composition, showed the advantages and effects described in the context of the present invention (see also the biological examples hereinbelow).

In a preferred embodiment, a composition according to the present invention is a composition, wherein
the total amount of component (i) is in the range of from 125 to 250 g/L,
and
the total amount of component (ii) is in the range of from 3 to 6 g/L,
in each case based on the total amount of the composition.

Own experiments have shown that compositions according to the present invention comprising a total amount of component (i) in the range of from 150 to 200 g/L, and a total amount of component (ii) in the range of from 4 to 6 g/L, in each case based on the total amount of the composition, are particularly suitable in the context of the present invention.

For example, a composition according to the present invention comprising a total amount of component (i) of about 150 g/L, and a total amount of component (ii) of about 4 g/L, in each case based on the total amount of the composition, showed the advantages and effects described in the context of the present invention (see also the biological examples hereinbelow).

The present invention preferably relates to the use of a combination of herbicides or to the use of a composition comprising a combination of herbicides as defined in the context of the present invention, in or on permanent cropland, or on permanent crops.

A permanent crop is one produced from plants which last for many seasons, rather than being replanted after each harvest. Permanent crops are grown on permanent crop land in the form of agricultural land that includes grasslands and shrublands, e.g. used to grow grape vines or coffee; orchards used to grow fruit or olives; and forested plantations, e.g. used to grow nuts or rubber. It does not include, however, tree farms intended to be used for wood or timber.

Preferred permanent croplands in the context of the present invention are plantations, grasslands and shrublands. Preferably, the permanent crops in the context of the present invention are plantation crops, and preferably are selected from the group consisting fruit crops and orchard crops (preferably fruit trees, citrus trees, mango trees, olive trees, grape vines, coffee, cocoa, tea, and berries (such as strawberries, raspberries, blueberries and currants)), *Musaceae* sp. crops (for example banana or plantain crops), nut trees (preferably almond trees, walnut trees, pistachio trees, pecan trees, hazelnut trees), oil palm trees, rubber trees, sugarcane and cotton.

More preferably, the permanent crops in the context of the present invention are fruit trees (preferably pome fruit trees and stone fruit trees; preferred fruit trees are apple trees, pear trees, apricot trees, plum trees, cherry trees, peach trees), olive trees, grape vines, coffee, tea), *Musaceae* sp. crops (preferably banana crops or plantain crops), nut trees (preferably almond trees, walnut trees, pistachio trees, pecan trees, hazelnut trees), oil palm trees, rubber trees, and citrus crops (preferably lemon, orange or grapefruit crops).

Even more preferably, the permanent crops in the context of the present invention are selected from the group consisting of apple trees, pear trees, apricot trees, plum trees, cherry trees, peach trees, olive trees, grape vines, coffee, tea, banana crops, nut trees (preferably almond trees, walnut trees, pistachio trees), oil palm trees, rubber trees, and citrus crops (preferably lemon, orange or grapefruit crops).

Particularly preferably, the permanent crops in the context of the present invention are selected from the group consisting of apple trees, pear trees, apricot trees, plum trees, cherry trees, peach trees, olive trees, grape vines, coffee, tea, banana crops, almond trees, walnut trees, oil palm trees, rubber trees, lemon crops, orange crops and grapefruit crops.

The herbicides used in the context of the present invention are known per se, and described inter alia in "The Pesticide Manual", 16th edition, The British Crop Protection Council and the Royal Soc. of Chemistry, 2012 and the literature cited therein. The herbicides used in the context of the present invention are described in more detail hereinbelow.

According to the present invention the expression "composition" includes compositions comprising a herbicide combination as defined herein, and can be used in various acceptable or agronomically typical forms and formulations, for example in a single "ready-mix" form.

The herbicides (i) and (ii) used in the herbicide combinations used in the context of the present invention and the compositions comprising the herbicide combinations used in the context of the present invention may be a combined spray mixture composed from separate formulations of the single active compounds, such as a "tank-mix", or said composition can be a combined use of the single active ingredients when applied in a sequential manner, i.e. one after the other within a reasonably short period, such as a few hours (and preferably less than 24 hours).

The salts of compounds used in the context of the present invention may be used in the form of the respective agronomically acceptable salts, such as alkali metal salts, alkaline earth salts or ammonium salts.

Component (i) of a herbicide combination according to the present invention is glufosinate and/or agronomically acceptable salts thereof.

Glufosinate (IUPAC-Name: (2RS)-2-amino-4[hydroxy(methyl)phosphinoyl]butyric acid or 4-[hydroxy(methyl)phosphinoyl]-DL-homoalanine, CAS Reg. No. 51276-47-2) and agronomically acceptable salts thereof are known, in particular glufosinate-ammonium (IUPAC-Name: ammonium (2RS)-2-amino-4-(methylphosphinato)butyric acid, CAS Reg. No. 77182-82-2).

Glufosinate is represented by the following structure (1):

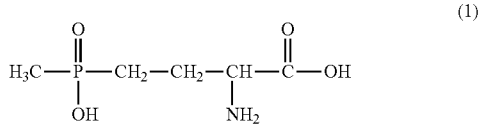

(1)

The compound of formula (1) is a racemate. Thus, in the context of the present invention, the term "glufosinate" only relates to glufosinate in racemic form.

Preferably, the agronomically acceptable salts of glufosinate are the sodium, potassium or ammonium ($NH_4^+$) salts of glufosinate, more preferably its sodium or ammonium salt, in particular glufosinate-ammonium.

Methods for producing (intermediates for the synthesis of) glufosinate are described for example in U.S. Pat. Nos. 4,521,348, 4,599,207 and 6,359,162B1.

Component (ii) of a herbicide combination according to the present invention is indaziflam (IUPAC-Name: $N^2$-[(1R,2S)-2,3-dihydro-2,6-dimethyl-1H-inden-1-yl]-6-[(1RS)-1-fluoroethyl]-1,3,5-triazine-2,4-diamine, CAS Reg. No. 950782-86-2, its (1*R)-1-fluoroethyl diastereoisomer, CAS Reg. No. 730979-19-8, and its (1*S)-1-fluoroethyl diastereoisomer CAS Reg. No. 730979-32-5) are known and described for example in WO 2004/069814 A1 and U.S. Pat. No. 6,069,114 A.

In the context of the present invention, component (ii) preferably refers to indaziflam, wherein the ratio by weight of the total amount of the (1*R)-1-fluoroethyl diastereoisomer of indaziflam is equal to or greater than the total amount of the (1*S)-1-fluoroethyl diastereoisomer of indaziflam, more preferably said ratio is greater than 2:1, more preferably greater than 3:1, even more preferably greater than 5:1, and particularly preferably greater than 10:1.

Most preferably in the context of the present invention, component (ii) only refers to the (1*R)-1-fluoroethyl diastereoisomer of indaziflam (CAS Reg. No. 730979-19-8), represented by the following structure (the (1*R)-1-fluoroethyl moiety is marked with an asterisk 1*R):

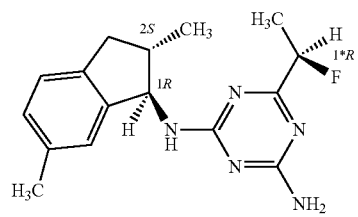 [SMILES: Cc1ccc2c(c1)[C@H](Nc1nc(N)nc([C@@H](C)F)n1)[C@@H](C)C2]

In accordance with the present invention, the herbicide combinations as defined herein or the composition comprising a herbicide combination as defined herein comprise a herbicidally effective amount of said herbicide combination and may comprise further components, for example agrochemically active compounds of a different type and/or formulation auxiliaries and/or additives customary in crop protection, or they may be employed together with these.

In accordance with the present invention, the herbicide combinations as defined herein or the composition comprising a herbicide combination as defined herein may be applied as a split application over time. Another possibility is the application of the individual herbicides (i) and (ii) or the herbicide combinations in a plurality of portions (sequential application).

Preferred is the simultaneous or nearly simultaneous application of the herbicides (i) and (ii) as defined herein. In the latter context, a nearly simultaneous application of the herbicides (i) and (ii) as defined herein means that the herbicide (i) glufosinate and/or agronomically acceptable salts thereof and the herbicide (ii) indaziflam are applied within 24 hours, preferably within 12 hours, more preferably within 6 hours, even more preferably within 3 hours.

In a particularly preferred embodiment, the herbicides (i) and (ii) as defined herein are used together, i.e. at the same time. Thus, in a particularly preferred embodiment, the compositions as defined in the context of the present invention are used.

The effects observed when using the herbicide combinations as defined according to the present invention or the compositions according to the present invention allow a more potent herbicidal action (in particular a higher/stronger initial herbicidal activity), an extended herbicidal activity period and/or a reduced number of required individual applications and—as a result—more advantageous weed control systems both from an economical and ecological point of view.

In a preferred embodiment, the herbicide combination (used) in accordance with the present invention or the composition comprising the herbicides (i) and (ii) (used) in accordance with the present invention is applied once, twice or three times per Gregorian calendar year, i.e. in one application, in two applications or in three applications per year according to the Gregorian calendar.

In a preferred embodiment, the herbicide combination (used) in accordance with the present invention or the composition comprising the herbicides (i) and (ii) (used) in accordance with the present invention is applied twice time per Gregorian calendar year, i.e. in two applications per year according to the Gregorian calendar.

In an alternatively preferred embodiment, the herbicide combination (used) in accordance with the present invention or the composition comprising the herbicides (i) and (ii)

(used) in accordance with the present invention is applied one time per Gregorian calendar year, i.e. in one application per year according to the Gregorian calendar.

In a preferred embodiment, the herbicide combination (used) in accordance with the present invention or the composition comprising the herbicides (i) and (ii) (used) in accordance with the present invention is applied one time in about 12 months, i.e. in one application in about 12 months.

The herbicide combinations according to the present invention and the compositions comprising the herbicides (i) and (ii) as defined in the context of the present invention are preferably used in post-emergence applications.

Furthermore, the herbicides (i) and (ii) as defined herein can be used together with other agrochemically active compounds, for example from the group of the safeners, fungicides, insecticides, other herbicides and other plant growth regulators, or with formulation auxiliaries and additives customary in crop protection. Additives are, for example, fertilizers and colorants.

The combination of herbicides as defined in the context of the present invention or the composition according to the present invention have an outstanding herbicidal activity against a broad spectrum of economically important harmful monocotyledonous and dicotyledonous harmful plants. Also here, post-emergence application is preferred.

Specifically, examples may be mentioned of some representatives of the monocotyledonous and dicotyledonous weed flora which can be controlled by the combinations according to the invention, without the enumeration being a restriction to certain species.

In the context of the present text, reference may be made to growth stages according to the BBCH monograph "Growth stages of mono- and dicotyledonous plants", $2^{nd}$ edition, 2001, ed. Uwe Meier, Federal Biological Research Centre for Agriculture and Forestry (Biologische Bundesanstalt für Land and Forstwirtschaft).

Examples of monocotyledonous harmful plants on which the herbicidal combinations and compositions according to the present invention act efficiently are from amongst the genera *Hordeum* spp., *Echinochloa* spp., *Poa* spp., *Bromus* spp., *Digitaria* spp., *Eriochloa* spp., *Setaria* spp., *Pennisetum* spp., *Eleusine* spp., *Eragrostis* spp., *Panicum* spp., *Lolium* spp., *Brachiaria* spp., *Leptochloa* spp., *Avena* spp., *Cyperus* spp., *Axonopris* spp., *Sorghum* spp., and *Melinus* spp.

Particular examples of monocotyledonous harmful plants species on which the herbicidal combinations and compositions according to the present invention act efficiently are selected from from amongst the species *Hordeum murinum*, *Echinochloa crus-galli*, *Poa annua*, *Bromus rubens* L., *Bromus rigidus*, *Bromus secalinus* L., *Digitaria sanguinalis*, *Eriochloa gracilis*, *Setaria faberi*, *Setaria viridis*, *Pennisetum glaucum*, *Eleusine indica*, *Eragrostis pectinacea*, *Panicum miliaceum*, *Lolium multiflorum*, *Brachiaria platyphylla*, *Leptochloa fusca*, *Avena fatua*, *Cyperus compressus*, *Cyperus esculentes*, *Axonopris offinis*, *Sorghum halapense*, and *Melinus repens*.

Examples of dicotyledonous harmful plants on which the herbicidal combinations and compositions according to the present invention act efficiently are from amongst the genera *Amaranthus* spp., *Polygonum* spp., *Medicago* spp., *Mollugo* spp., *Cyclospermum* spp., *Stellaria* spp., *Gnaphalium* spp., *Taraxacum* spp., *Oenothera* spp., *Amsinckia* spp., *Erodium* spp., *Erigeron* spp., *Senecio* spp., *Lamium* spp., *Kochia* spp., *Chenopodium* spp., *Lactuca* spp., *Malva* spp., *Ipomoea* spp., *Brassica* spp., *Sinapis* spp., *Urtica* spp., *Sida* spp, *Portulaca* spp., *Richardia* spp., *Ambrosia* spp., *Calandrinia* spp., *Sisymbrium* spp., *Sesbania* spp., *Capsella* spp., *Sonchus* spp., *Euphorbia* spp., *Helianthus* spp., *Coronopus* spp., *Salsola* spp., *Abutilon* spp., *Vicia* spp., *Epilobium* spp., *Cardamine* spp., *Picris* spp., *Trifolium* spp., *Galinsoga* spp., *Epimedium* spp., *Marchantia* spp., *Solanum* spp., *Oxalis* spp., *Metricaria* spp., *Plantago* spp., *Tribulus* spp., *Cenchrus* spp. *Bidens* spp., *Veronica* spp., and *Hypochaeris* spp.

Particular examples of dicotyledonous harmful plants species on which the herbicidal combinations and compositions according to the present invention act efficiently are selected from amongst the species *Amaranthus spinosus*, *Polygonum convolvulus*, *Medicago polymorpha*, *Mollugo verticillata*, *Cyclospermum leptophyllum*, *Stellaria media*, *Gnaphalium purpureum*, *Taraxacum offi cinale*, *Oenothera laciniata*, *Amsinckia intermedia*, *Erodium cicutarium*, *Erodium moschatum*, *Erigeron bonariensis*, *Senecio vulgaris*, *Lamium amplexicaule*, *Erigeron canadensis*, *Polygonum aviculare*, *Kochia scoparia*, *Chenopodium album*, *Lactuca serriola*, *Malva parviflora*, *Malva neglecta*, *Ipomoea hederacea*, *Ipomoea lacunose*, *Brassica nigra*, *Sinapis arvensis*, *Urtica dioica*, *Amaranthus blitoides*, *Amaranthus retroflexus*, *Amaranthus hybridus*, *Amaranthus lividus*, *Sida spinosa*, *Portulaca oleracea*, *Richardia scabra*, *Ambrosia artemisiifolia*, *Calandrinia caulescens*, *Sisymbrium irio*, *Sesbania exaltata*, *Capsella bursa-pastoris*, *Sonchus oleraceus*, *Euphorbia maculate*, *Helianthus annuus*, *Coronopus didymus*, *Salsola tragus*, *Abutilon theophrasti*, *Vicia benghalensis* L., *Epilobium paniculatum*, *Cardamine* spp, *Picris echioides*, *Trifolium* spp., *Galinsoga* spp., *Epimedium* spp., *Marchantia* spp., *Solanum* spp., *Oxalis* spp., *Metricaria matriccarioides*, *Plantago* spp., *Tribulus terrestris*, *Salsola kali*, *Cenchrus* spp. *Bidens bipinnata*, *Veronica* spp., and *Hypochaeris radicata*.

As shown in the biological examples hereinbelow, for example the following harmful plants or undesired plants are controlled in a more effective and superior manner by application of the herbicidal combinations and compositions according to the present invention when compared to glufosinate alone: *Amaranthus retroflexus*, *Stellaria media*, *Lolium multiflorum* and *Poa annua*.

As shown in the biological field trial examples hereinbelow, for example the following harmful plants or undesired plants are controlled in a more effective and superior manner by application of the herbicidal combinations and compositions according to the present invention when compared to glufosinate alone: *Amaranthus blitoides*, *Amaranthus lividus*, *Chenopodium album*, *Cyperus esculentes*, *Digitaria sanguinalis*, *Eleusine indica*, *Euphorbia maculata*, *Erigeron bonariensis*, *Erigeron canadensis*, *Erodium moschatum*, *Malva neglecta*, *Mollugo verticillata*, *Salsola kali* subsp. *ruthenica*, *Scoparia dulcis*, *Poa annua* and *Polygonum aviculare*.

If the herbicide combinations according to the present invention and the compositions according to the present invention are applied post-emergence to the green parts of the plants, growth likewise stops drastically a very short time after the treatment and the weed plants remain at the growth stage of the point of time of application, or they die completely after a certain time, so that in this manner competition by the weeds, which is harmful to the crops, is eliminated at a very early point in time and in a sustained manner.

The herbicide combinations according to the present invention and the compositions according to the present invention are characterized by a rapidly commencing and long-lasting herbicidal action. As a rule, the rainfastness of the active compounds in the herbicide combinations according to the present invention is advantageous. A particular advantage is that the dosages of the herbicides (i) and (ii) as defined in the context of the present invention can be adjusted to such a low quantity that their soil action is low. This also allows them to be employed in sensitive crops (such as (young) plantation crops). Also, the combination of herbicides (i) and (ii) as defined in the context of the present invention allows the application rate of the herbicides (i) and (ii) required to be reduced.

In particular when the herbicide combinations as defined in the context of the present invention and the compositions comprising a herbicide combination as defined in the context of the present invention are employed application rates may be reduced, a broader spectrum of broad-leaved weeds and grass weeds maybe controlled, the herbicidal action may take place more rapidly, the duration of action may be longer, the harmful plants may be controlled better while using only one, or few, applications, and the application period which is possible to be extended.

The abovementioned properties and advantages are of benefit for weed control practice to keep agricultural crops free from undesired competing plants and thus to safeguard and/or increase the yields from the qualitative and/or quantitative point of view. These novel combinations markedly exceed the technical state of the art with a view to the properties described.

Owing to their herbicidal and plant-growth-regulatory properties, the compositions according to the present invention can be employed for controlling harmful plants in genetically modified crops or crops obtained by mutation/selection. These crops are distinguished as a rule by particular, advantageous properties, such as resistances to herbicidal compositions or resistances to plant diseases or causative agents of plant diseases such as particular insects or microorganisms such as fungi, bacteria or viruses. Other particular properties relate, for example, to the harvested material with regard to quantity, quality, storability, composition and specific constituents. Thus, for example, transgenic plants are known whose starch content is increased or whose starch quality is altered, or those where the harvested material has a different fatty acid composition.

The present invention also relates to a method of controlling undesired vegetation (e.g. harmful plants), which comprises applying a herbicide combination and compositions as defined in the context of the present invention or applying a composition as defined in the context of the present invention, preferably by the post-emergence method, to harmful or undesired plants, parts of said harmful or undesired plants, or the area where the harmful or undesired plants grow, for example the area under cultivation.

In the context of the present invention "controlling" denotes a significant reduction of the growth of the harmful plant(s) in comparison to the untreated harmful plants. Preferably, the growth of the harmful plant(s) is essentially diminished (60-79%), more preferably the growth of the harmful plant(s) is largely or fully suppressed (80-100%), and in particular the growth of the harmful plant(s) is almost fully or fully suppressed (90-100%).

Thus, in a further aspect, the present invention relates to a method for
controlling undesired plant growth,
and/or
controlling harmful plants,
comprising the step of applying a combination of herbicides according to the present invention (preferably in one of the preferred embodiments defined herein) or a composition according to the present invention (preferably in one of the preferred embodiments defined herein) onto the undesired plants or the harmful plants, on parts of the undesired plants or the harmful plants, or on the area where the undesired plants or the harmful plants grow.

The preferred application rates [indicated as g/ha i.e. grams of active ingredient per hectare] of the herbicides (components (i) and (ii)) used in the context of the present invention as defined herein are as follows.

In a preferred method for controlling undesired plant growth and/or for controlling harmful plants, the total amount per hectare per Gregorian calendar year of component (i) glufosinate and the agronomically acceptable salts thereof does not exceed 1500 g, and preferably does not exceed 1250 g.

In many cases it is preferred in the context of a method for controlling undesired plant growth, and/or for controlling harmful plants according to the present invention that the total amount per hectare per Gregorian calendar year of component (i) glufosinate and the agronomically acceptable salts thereof does not exceed 1000 g, more preferably does not exceed 800 g, and even more preferably does not exceed 750 g.

In a preferred method for controlling undesired plant growth and/or for controlling harmful plants, the total amount per hectare per Gregorian calendar year of component (ii) indaziflam does not exceed 30 g, and preferably does not exceed 25 g.

These lower amounts of component (ii) indaziflam are particularly suitable to achieve the surprising and desired aspects (c), (d) and/or (e) mentioned above in the context of the present invention.

In a particularly preferred method for controlling undesired plant growth and/or for controlling harmful plants, the total amount per hectare per Gregorian calendar year of component (i) glufosinate and the agronomically acceptable salts thereof does not exceed 1250 g (and preferably does not exceed 1000 g), and the total amount per hectare per Gregorian calendar year of component (ii) indaziflam does not exceed 25 g.

In a more particularly preferred method for controlling undesired plant growth and/or for controlling harmful plants, the total amount per hectare per Gregorian calendar year of component (i) glufosinate and the agronomically acceptable salts thereof does not exceed 1000 g (and preferably does not exceed 750 g), and the total amount per hectare per Gregorian calendar year of component (ii) indaziflam does not exceed 24 g.

Preferably, the combinations of herbicides according to the present invention as defined herein or the compositions according to the present invention as defined herein are applied in a method for controlling undesired plant growth and/or for controlling harmful plants on permanent crops and/or on permanent crop land. Preferably, the permanent crops in the context of the present invention are plantation crops, and preferably are selected from the group consisting fruit crops and orchard crops (preferably fruit trees, citrus trees, mango trees, olive trees, grape vines, coffee, cocoa, tea, and berries (such as strawberries, raspberries, blueberries and currants)), *Musaceae* sp. crops (for example banana or plantain crops), nut trees (preferably almond trees, walnut trees, pistachio trees, pecan trees, hazelnut trees), oil palm trees, rubber trees, sugarcane and cotton. Even more preferably, the permanent crops in the context of the present invention are those mentioned above as even more preferred permanent crops, particularly preferably, the permanent crops in the context of the present invention are those mentioned above as particularly preferred permanent crops.

As already mentioned above, the herbicide combinations as defined in the context of the present invention can not only be used as mixed formulations, if appropriate together with further agrochemically active compounds, additives and/or customary formulation auxiliaries, which are then applied in the customary manner as a dilution with water, but also as so-called tank mixes by jointly diluting the separately formulated, or partially separately formulated, components with water.

The herbicide combinations as defined in the context of the present invention and the compositions comprising a herbicide combination as defined in the context of the present invention can be formulated in various ways, depending on the prevailing biological and/or chemical-physical parameters. The following are examples of general possibilities for formulations: wettable powders (WP), water-soluble concentrates, emulsifiable concentrates (EC), aqueous solutions (SL), emulsions (EW) such as oil-in-water and water-in-oil emulsions, sprayable solutions or emulsions, suspension concentrates (SC), oil dispersions (OD), oil- or water-based dispersions, suspoemulsions, dusts (DP), seed-dressing materials, granules for soil application or for broadcasting, or water-dispersible granules (WG), ULV formulations, microcapsules or waxes.

Herbicidal formulations comprising glufosinate or saltes thereof salts such as glufosinate-ammonium, are well known in the art, for example, from EP 0048436, EP 0336151 A2, U.S. Pat. Nos. 5,258,358, 5,491,125, US 2005/0266995 A1, US 2005/0266998 A1, US 2005/266999 A1, US 2007/0184982 A1 or US 2008/0045415 A1, and such formulations are suitable in the context of the present invention.

Preferably, the herbicidal combinations according to the present invention (preferably in one of the preferred embodiments defined herein) and compositions according to the present invention (preferably in one of the preferred embodiments defined herein) are used in the form of suspension concentrates (SC), oil dispersions (OD), or microcapsules.

Preferably, the a combination of herbicides according to the present invention (preferably in one of the preferred embodiments defined herein) and the compositions according to the present invention (preferably in one of the preferred embodiments defined herein) are easily and readily obtained, by combining the components (i) and (ii) in the ratio by weight as defined in the context of the present invention, for example by mixing the appropriate amounts if components (i) and (ii).

Thus, in a further aspect, the present invention relates to a method for producing a combination of herbicides according to the present invention (preferably in one of the preferred embodiments defined herein) and to a method of producing the compositions according to the present invention (preferably in one of the preferred embodiments defined herein), comprising the steps of
(a) providing component (i),
(b) providing component (ii), and
(c) combining component (i) and component (ii),
such that a combination of herbicides according to the present invention (preferably in one of the preferred embodiments defined herein) or a composition according to the present invention (preferably in one of the preferred embodiments defined herein) is obtained.

The individual formulation types are known in principle and are described for example, in: Winnacker-Küchler, "Chemische Technologie", Volume 7, C. Hauser Verlag Munich, 4$^{th}$ Edition, 1986; van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries required, such as inert materials, surfactants, solvents and other additives are also known and are described, for example, in Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y. Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschaft, Stuttgart 1976, Winnacker-Küchler, "Chemische Technologie", Volume 7, C. Hauser Verlag Munich, 4$^{th}$ Edition 1986.

Based on these formulations, combinations with other agrochemically active substances, such as other herbicides not belonging to constituents (i) and (ii) as defined in the context of the present invention, fungicides or insecticides, and with safeners, fertilizers and/or growth regulators, may also be prepared, for example in the form of a readymix or a tank mix.

Wettable powders (sprayable powders) are products which are uniformly dispersible in water and which, besides the active compound, also comprise ionic or nonionic surfactants (wetters, dispersants), for example polyoxethylated alkylphenols, polyethoxylated fatty alcohols or fatty amines, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoyl-methyltauride, in addition to a diluent or inert material.

Emulsifiable concentrates are prepared by dissolving the active compound in an organic solvent, for example butanol, cyclohexanone, dimethylformamide, xylene or else higher-boiling aromatics or hydrocarbons with addition of one or more ionic or nonionic surfactants (emulsifiers). Examples of emulsifiers which may be used are: calcium salts of alkylarylsulfonic acids, such as calcium dodecylbenzene sulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxethylene sorbitol esters.

Dusts are obtained by grinding the active compound with finely divided solid materials, for example talc, natural clays such as kaolin, bentonite and pyrophyllite, or diatomaceous earth.

Suspension concentrates (SC) can be water- or oil-based. They can be prepared, for example, by wet grinding by means of commercially available bead mills and, if appropriate, addition of further surfactants as they have already been mentioned for example above in the case of the other formulation types.

Emulsions, for example oil-in-water emulsions (EW), can be prepared for example by means of stirrers, colloid mills and/or static mixers using aqueous organic solvents and, if appropriate, further surfactants as have already been mentioned for example above in the case of the other formulation types.

Granules can be prepared either by spraying the active compound onto adsorptive, granulated inert material or by applying active compound concentrates to the surface of carriers such as sand, kaolinites or granulated inert material with the aid of binders, for example polyvinyl alcohol, sodium polyacrylate or else mineral oils. Suitable active compounds may also be granulated in the manner conventionally used for the production of fertilizer granules, if desired in a mixture with fertilizers. As a rule, water-dispersible granules are prepared by customary processes such as spray drying, fluidized-bed granulation, disk granulation, mixing with high-speed mixers and extrusion without solid inert material. Regarding the production of disk granules, fluidized-bed granules, extruder granules and spray granules, see, for example, the methods in "Spray-Drying Handbook" 3rd ed. 1979, G. Goodwin Ltd., London; J. E. Browning, "Agglomeration", Chemical and Engineering 1967, page 147 et seq; "Perry's Chemical Engineer's Handbook", 5th Ed., McGraw-Hill, New York 1973, pp. 8-57.

As regards further details on the formulation of crop protection products, see, for example, G. C. Klingmam, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical formulations comprise 1 to 95% by weight, of active compounds, the following concentrations being customary, depending on the type of formulation:

The active compound concentration in wettable powders is, for example, approximately 10 to 95% by weight, the remainder to 100% by weight being composed of customary formulation constituents. In the case of emulsifiable concentrates, the active compound concentration may amount to, for example, 5 to 80% by weight. Formulations in the form of dusts comprise, in most cases, 5 to 20% by weight of active compound, sprayable solutions approximately 0.2 to 25% by weight of active compound. In the case of granules such as dispersible granules, the active compound content depends partly on whether the active compound is present in liquid or solid form and on which granulation auxiliaries and fillers are being used. As a rule, the content amounts to between 10 and 90% by weight in the case of the water-dispersible granules.

In addition, the abovementioned active compound formulations may comprise, if appropriate, the conventional adhesives, wetters, dispersants, emulsifiers, preservatives, antifreeze agents, solvents, fillers, colorants, carriers, antifoams, evaporation inhibitors, pH regulators or viscosity regulators.

The herbicidal action of the herbicide combinations according to the present invention can be improved, for example, by surfactants, preferably by wetters from the group of the fatty alcohol polyglycol ethers. The fatty alcohol polyglycol ethers preferable contain 10-18 carbon atoms in the fatty alcohol radical and 2-20 ethylene oxide units in the polyglycol ether moiety. The fatty alcohol polyglycol ethers can be nonionic or ionic, for example in the form of fatty alcohol polyglycol ethers sulfates, which can be used, for example, as alkali metal salts (e.g. sodium salts or potassium salts) or ammonium salts, but also as alkaline earth metal salts such as magnesium salts, such as sodium $C_{12}/C_{14}$-fatty alcohol diglycol ether sulfate (Genapol® LRO, Clariant); see, for example, EP-A-0476555, EP-A-0048436, EP-A-0336151 or U.S. Pat. No. 4,400,196 and also Proc. EWRS Symp. "Factors Affecting Herbicidal Activity and Selectivity", 227-232 (1988). Nonionic fatty alcohol polyglycol ethers are, for example, $(C_{10}-C_{18})$-, preferably $(C_{10}-C_{14})$-fatty alkohol polyglycol ethers containing 2-20, preferably 3-15, ethylene oxide units (e.g. isotridecyl alcohol polyglycol ether), for example from the Genapol® series, such as Genapol® X-030, Genapol® X-060, Genapol® X-080 or Genapol® X-150 (all from Clariant GmbH).

The present invention furthermore embraces the combination of herbicides (i) and (ii) as defined above with the wetting agents mentioned above from the group of the fatty alcohol polyglycolethers which preferably contain 10-18 carbon atoms in the fatty alcohol radical and 2-20 ethylene oxide units in the polyglycol ether moiety and which can be present in nonionic or ionic form (for example as fatty alcohol polyglycol ether sulfates). Preference is given to $C_{12}/C_{14}$-fatty alcohol diglycol ether sulfate sodium (Genapol® LRO, Clariant); and isotridecyl alcohol polyglycol ether with 3-15 ethylene oxide units, for example from the Genapol® X series, such as Genapol® X-030, Genapol® X-060, Genapol® X-080 or Genapol® X-150 (all from Clariant GmbH). It is furthermore known that fatty alcohol polyglycol ethers such as nonionic or ionic fatty alcohol polyglycol ethers (for example fatty alcohol polyglycol ether sulfates) are also suitable for use as penetrants and activity enhancers for a number of other herbicides, inter alia also for herbicides from the group of the imidazolinones (see, for example, EP-A-0502014).

Moreover, it is known that fatty alcohol polyglycol ethers such as nonionic or ionic fatty alcohol polyglycol ethers (for example fatty alcohol polyglycol ether sulfates) are also suitable as penetrants and synergists for a number of other herbicides, inter alia also herbicides from the group of the imidazolinones; (see, for example, EP-A-0502014).

The herbicidal effect of the herbicide combinations according to the present invention can also be increased using vegetable oils. The term vegetable oils is to be understood as meaning oils from oil-plant species, such as soya oil, rapeseed oil, corn oil, sunflower oil, cottonseed oil, linseed oil, coconut oil, palm oil, safflower oil or castor oil, in particular rapeseed oil, and their transesterification products, for example alkyl esters, such as rapeseed oil methyl ester or rapeseed oil ethyl ester.

The vegetable oils are preferably esters of $C_{10}$-$C_{22}$-, preferably $C_{12}$-$C_{20}$-fatty acids. The $C_{10}$-$C_{22}$-fatty acid esters are, for example, esters of unsaturated or saturated $C_{10}$-$C_{22}$-fatty acids, in particular those with an even number of carbon atoms, for example erucic acid, lauric acid, palmitic acid and, in particular, $C_{18}$-fatty acids such as stearic acid, oleic acid, linoleic acid or linolenic acid.

Preferred $C_1$-$C_{20}$-alkyl-$C_{10}$-$C_{22}$-fatty acid esters are the methyl, ethyl, propyl, butyl, 2-ethylhexyl and dodecyl esters. Preferred glycol- and glycerol-$C_{10}$-$C_{22}$-fatty acid esters are the uniform or mixed glycol esters and glycerol esters of $C_{10}$-$C_{22}$-fatty acids, in particular those fatty acids which have an even number of carbon atoms, for example erucic acid, lauric acid, palmitic acid and, in particular, $C_{18}$-fatty acids such as stearic acid, oleic acid, linolic acid or linolenic acid.

The vegetable oils can be present in the herbicidal compositions according to the present invention for example in the form of commercially available oil-containing formulation additives, in particular those based on rapeseed oil such as Hasten® (Victorian Chemical Company, Australia, hereinbelow termed Hasten, main constituent: rapeseed oil ethyl ester), Actirob® B (Novance, France, hereinbelow termed ActirobB, main constituent: rapeseed oil methyl ester), Rako-Binol® (Bayer AG, Germany, termed Rako-Binol hereinbelow, main constituent: rapeseed oil), Renol® (Stefes, Germany, termed Renol hereinbelow, vegetable oil constituent: rapeseed oil methyl ester), or Stefes Mero® (Stefes, Germany, hereinbelow termed Mero, main constituent: rapeseed oil methyl ester).

In a further embodiment, the present invention embraces the combination of a herbicide combination as defined in the context of the present invention with the vegetable oils mentioned above. Thus, in a further embodiment, the present invention embraces the use of compositions comprising a herbicide combination as defined in the context of the present invention comprising the vegetable oils mentioned above, such as rapeseed oil, preferably in the form of commercially available oil-containing formulation additives, in particular those based on rapeseed oil such as Hasten® (Victorian Chemical Company, Australia, hereinbelow termed Hasten, main constituent: rapeseed oil ethyl ester), Actirob® B (Novance, France, hereinbelow termed ActirobB, main constituent: rapeseed oil methyl ester), Rako-Binol® (Bayer AG, Germany, termed Rako-Binol hereinbelow, main constituent: rapeseed oil), Renol® (Stefes, Germany, termed Renol hereinbelow, vegetable oil constituent: rapeseed oil methyl ester), or Stefes Mero® (Stefes, Germany, hereinbelow termed Mero, main constituent: rapeseed oil methyl ester).

For use, the formulations, which are present in commercially available form, are optionally diluted in the customary manner, for example using water in the case of wettable powders, emulsifiable concentrates, dispersions and water-dispersible granules. Preparations in the form of dusts, soil granules, granules for broadcasting and sprayable solutions are usually not diluted further with other inert substances prior to use.

A herbicide combination according to the present invention and a composition comprising the herbicide combination as defined in the context of the present invention are preferably applied to the harmful plants or undesired plants or parts thereof, seeds of the plants or the area under cultivation (soil of a field), preferably to the green of the harmful plants or parts thereof, or to the green parts of the undesired plants or parts thereof.

A composition comprising a herbicide combination used in the context of the present invention has the advantage of being easier to apply since the quantities of the components are already presented in the correct ratio to each other. Moreover, the adjuvants in the formulation can be matched optimally to each other.

As already described in more detail above, the present invention further relates to the use of combination of herbicides according to the present invention (preferably in one of the preferred embodiments defined herein) or a composition according to the present invention (preferably in one of the preferred embodiments defined herein) in the field of agriculture, in particular as plant growth regulators and/or for controlling harmful plants or undesired plant growth.

EXAMPLES

1. Products Used

The following products were used in the biological trials described hereinafter:

Product P1 contained 150 g/L of glufosinate-ammonium (i.e. in racemic form), not in accordance with the present invention.

Product P2 contained 150 g/L of glufosinate-ammonium (i.e. in racemic form) and 4 g/L of indaziflam [the ratio by weight of the (1*R)-1-fluoroethyl diastereoisomer of indaziflam to the ratio by weight of the (1*S)-1-fluoroethyl diastereoisomer of indaziflam was about 95:5].

It is known that indaziflam shows insufficient post-emergence efficacy on monocotyledonous and dicotyledonous harmful plant species. Correspondingly, a product containing 4 g/L of indaziflam [the ratio by weight of the (1*R)-1-fluoroethyl diastereoisomer of indaziflam to the ratio by weight of the (1*S)-1-fluoroethyl diastereoisomer of indaziflam was about 95:5] showed only very limited post-emergence efficacy on monocotyledonous and dicotyledonous harmful plant species, if any.

Product P3 contained 250 g/L of glufosinate-ammonium (i.e. in racemic form), not in accordance with the present invention.

Product P4 contained 250 g/L of glufosinate-ammonium (i.e. in racemic form) and 7.5 g/L of indaziflam [the ratio by weight of the (1*R)-1-fluoroethyl diastereoisomer of indaziflam to the ratio by weight of the (1*S)-1-fluoroethyl diastereoisomer of indaziflam was about 95:5].

2. Biological Trials

In separate pots, biological trials were conducted in the greenhouse under identical conditions (apart from the treatment with the different products P1 and P2 mentioned above). Each pot contained the same soil and the same amount of seeds of each of the following weeds (two monocotyledonous and two dicotyledonous harmful plant species (weed species)):

| Code | Weed species Scientific Name |
| --- | --- |
| AMARE | *Amaranthus retroflexus* |
| STEME | *Stellaria media* |
| LOLMU | *Lolium multiflorum* |
| POAAN | *Poa annua* |

Tables 1 to 4 reflect the respective observed herbicidal activity ratings after treatment of the monocotyledonous harmful plant species (BBCH growth stage 11) and dicotyledonous harmful plant species (BBCH growth stage 10) for the different products applied once in post-emergence.

The observation period in each case was 40 days after start of treatment with the respective products P1 and P2 mentioned above, both in amounts of 3 L/ha and 5 L/ha, respectively.

TABLE 1

Ratings of herbicidal activity against the above-mentioned harmful plant species after a single post-emergence treatment in an amount of 450 g/ha of glufosinate-ammonium (corresponding to 3 L/ha of product P1)

| Weed | Initial herbicidal activity | Regrowth |
| --- | --- | --- |
| AMARE | medium | after 5 days strong regrowth |
| STEME | weak | after 3 days strong regrowth |
| LOLMU | weak | after 2 days strong regrowth |
| POAAN | medium | after 3 days strong regrowth |

TABLE 2

Ratings of herbicidal activity against the above-mentioned harmful plant species after a single post-emergence treatment in an amount of 450 g/ha of glufosinate-ammonium and 12 g/ha indaziflam (corresponding to 3 L/ha of product P2)

| Weed | Initial herbicidal activity | Regrowth |
| --- | --- | --- |
| AMARE | strong | no regrowth |
| STEME | strong | no regrowth |
| LOLMU | strong | after 9 days weak regrowth |
| POAAN | strong | no regrowth |

TABLE 3

Ratings of herbicidal activity against the above-mentioned harmful plant species after a single post-emergence treatment in an amount of 750 g/ha of glufosinate-ammonium (corresponding to 5 L/ha of product P1)

| Weed | Regrowth |
| --- | --- |
| AMARE | no regrowth |
| STEME | after 9 days weak regrowth |
| LOLMU | after 5 days strong regrowth |
| POAAN | after 8 days strong regrowth |

TABLE 4

Ratings of herbicidal activity against the above-mentioned harmful plant species after a single post-emergence treatment in an amount of 750 g/ha of glufosinate-ammonium and 20 g/ha indaziflam (corresponding to 5 L/ha of product P2)

| Weed | Regrowth |
| --- | --- |
| AMARE | no regrowth |
| STEME | no regrowth |
| LOLMU | no regrowth |
| POAAN | no regrowth |

Tables 5 to 8 reflect the respective observed herbicidal activity ratings after treatment of the monocotyledonous harmful plant species (BBCH growth stage 12-13) and dicotyledonous harmful plant species (BBCH growth stage 12) for the different products applied once in post-emergence. The observation period in each case was 40 days after start of treatment with the respective products P1 and P2 mentioned above, both in amounts of 3 L/ha and 5 L/ha, respectively.

TABLE 5

Ratings of herbicidal activity against the above-mentioned harmful plant species after a single post-emergence treatment in an amount of 450 g/ha of glufosinate-ammonium (corresponding to 3 L/ha of product P1)

| Weed | Regrowth |
| --- | --- |
| AMARE | no regrowth |
| STEME | after 9 days very weak regrowth |
| LOLMU | after 8 days strong regrowth |
| POAAN | after 10 days strong regrowth |

TABLE 6

Ratings of herbicidal activity against the above-mentioned harmful plant species after a single post-emergence treatment in an amount of 450 g/ha of glufosinate-ammonium and 12 g/ha indaziflam (corresponding to 3 L/ha of product P2)

| Weed | Regrowth |
| --- | --- |
| AMARE | no regrowth |
| STEME | no regrowth |
| LOLMU | after 11 days medium regrowth |
| POAAN | after 16 days weak regrowth |

TABLE 7

Ratings of herbicidal activity against the above-mentioned harmful plant species after a single post-emergence treatment in an amount of 750 g/ha of glufosinate-ammonium (corresponding to 5 L/ha of product P1)

| Weed | Regrowth |
| --- | --- |
| AMARE | no regrowth |
| STEME | no regrowth |
| LOLMU | after 8 days strong regrowth |
| POAAN | after 12 days strong regrowth |

TABLE 8

Ratings of herbicidal activity against the above-mentioned harmful plant species after a single post-emergence treatment in an amount of 750 g/ha of glufosinate-ammonium and 20 g/ha indaziflam (corresponding to 5 L/ha of product P2)

| Weed | Regrowth |
| --- | --- |
| AMARE | no regrowth |
| STEME | no regrowth |
| LOLMU | after 23 days very weak regrowth |
| POAAN | no regrowth |

Table 9 reflects the post-emergence efficacy of indaziflam [the ratio by weight of the (1*R)-1-fluoroethyl diastereoisomer of indaziflam to the ratio by weight of the (1*S)-1-fluoroethyl diastereoisomer of indaziflam was about 95:5] on the above mentioned weeds (two monocotyledonous and two dicotyledonous harmful plant species (weed species)) AMARE, STEME, LOLMU and POOAN, each at BBCH growth stage 11-12. Indaziflam was used in an amount of 12 g/ha.

TABLE 9

Ratings of herbicidal activity against the above-mentioned harmful plant species after a single post-emergence treatment in an amount of 12 g/ha of indaziflam

| Weed | Regrowth |
| --- | --- |
| AMARE | very weak herbicidal effect starting on day 7 after treatment |
| STEME | no herbicidal effect |
| LOLMU | no herbicidal effect |
| POAAN | no herbicidal effect |

3. Biological Field Trials

In several different locations, biological field trials were conducted in neighbouring plots under identical conditions (apart from the treatment with the different products P3 and P4 mentioned above). Depending on the location, different harmful plant species (weed species) were present and the activity of products P3 and P4 against the different weed species was assessed.

The amount of products P3 and P4 in each biological field trial was such that 750 g/ha of glufosinate-ammonium were used.

The ratings of the herbicidal activity were performed on a scale of 0-100%, wherein 100% activity means that all weed plants had died in the respective plot, 50% herbicidal activity means that the weed coverage in the respective plot has been reduced by 50% in comparison to the untreated control plot, and 0% activity means that no herbicidal activity was observed in the respective plot in comparison to the untreated control plot.

The following Tables 10-13 show the ratings of herbicidal activity against different harmful plant species in the different locations after a single post-emergence treatment in an amount of 750 g/ha of glufosinate-ammonium (corresponding to 3 L/ha of product P3) and of 750 g/ha of glufosinate-ammonium and 22.5 g/ha of indaziflam (corresponding to 3 L/ha of product P4), respectively.

The following codes are used for the different harmful plant species (weed species):

| Code | Weed species Scientific Name |
|---|---|
| AMABL | *Amaranthus blitoides* |
| AMALI | *Amaranthus lividus* |
| CHEAL | *Chenopodium album* |
| CYPES | *Cyperus esculentes* |
| DIGSA | *Digitaria sanguinalis* |
| ELEIN | *Eleusine indica* |
| EPHMA | *Euphorbia maculata* |
| ERIBO | *Erigeron bonariensis* |
| ERICA | *Erigeron canadensis* |
| EROMO | *Erodium moschatum* |
| MALNE | *Malva neglecta* |
| MOLVE | *Mollugo verticillata* |
| SASKR | *Salsola kali* subsp. *ruthenica* |
| SCDFU | *Scoparia dulcis* |
| POAAN | *Poa annua* |
| POLAV | *Polygonum aviculare* |

TABLE 10

Ratings of herbicidal activity against harmful plant species 123 days after a single post-emergence treatment with product P3 and P4, respectively, in field plots in Colusa County, California

| Weed | Product P3 | Product P4 |
|---|---|---|
| CHEAL | 4% | 98% |
| ERIBO | 53% | 70% |
| MALNE | 65% | 83% |
| POLAV | 31% | 60% |

TABLE 11a

Ratings of herbicidal activity against harmful plant species 15 days after a single post-emergence treatment with product P3 and P4, respectively, in field plots in Hardee County, Florida

| Weed | Product P3 | Product P4 |
|---|---|---|
| AMALI | 80% | 93% |
| DIGSA | 40% | 57% |
| ELEIN | 54% | 64% |
| MOLVE | 67% | 77% |
| SCDFU | 47% | 67% |
| All Weed species present (average) | 50% | 70% |

TABLE 11b

Ratings of herbicidal activity against harmful plant species 56 days after a single post-emergence treatment with product P3 and P4, respectively, in field plots in Hardee County, Florida

| Weed | Product P3 | Product P4 |
|---|---|---|
| AMALI | 100% | 100% |
| DIGSA | 13% | 50% |
| ELEIN | 57% | 68% |
| MOLVE | 68% | 87% |
| SCDFU | 73% | 63% |
| All Weed species present (average) | 32% | 50% |

TABLE 12

Ratings of herbicidal activity against harmful plant species 90 days after a single post-emergence treatment with product P3 and P4, respectively, in field plots in San Joaquin County, California

| Weed | Product P3 | Product P4 |
|---|---|---|
| ERICA | 0% | 84% |
| EROMO | 7% | 100% |
| POAAN | 0% | 55% |

TABLE 13

Ratings of herbicidal activity against harmful plant species 31 days after a single post-emergence treatment with product P3 and P4, respectively, in field plots in Fresno County, California

| Weed | Product P3 | Product P4 |
|---|---|---|
| AMABL | 0% | 33% |
| CYPES | 33% | 67% |
| EPHMA | 0% | 33% |
| SASKR | 0% | 100% |

The invention claimed is:

1. An herbicidal composition comprising
   (i) glufosinate and/or an agronomically acceptable salt thereof,
   and
   (ii) indaziflam,
   wherein the ratio by weight of the total amount of component (i) to the total amount of component (ii) is in a range of from 25:1 to 50:1 based on the total amount of the composition;
   wherein components (i) and (ii) are the only agriculturally active components wherein the components (i) and (ii) together provide better herbicidal activity than (i) or (ii) alone.

2. The herbicidal composition according to claim 1, wherein the ratio by weight of the total amount of component (i) to the total amount of component (ii) in the herbicidal composition is in the range of from 30:1 to 50:1.

3. The herbicidal composition according to claim 1, wherein the ratio by weight of the total amount of component (i) to the total amount of component (ii) in the herbicidal composition is in the range of from 30:1 to 40:1.

4. The herbicidal composition according to claim 1, wherein the total amount of component (i) is equal to or less than 600 g/L, based on the total amount of the composition.

5. The herbicidal composition according to claim 1, wherein the total amount of component (ii) is in the range of from 2 to 20 g/L based on the total amount of the composition.

6. The herbicidal composition according to claim 1, wherein
   the total amount of component (i) is in the range of from 125 to 300 g/L,
   and
   the total amount of component (ii) is in the range of from 3 to 10 g/L,
   in each case based on the total amount of the composition.

7. The herbicidal composition according to claim 1, wherein the composition additionally comprises one or more further components selected from the group consisting of formulation auxiliaries, additives customary in crop protection, and further agrochemically active compounds.

8. The herbicidal composition according to claim 1, wherein the composition in the form of a suspension concentrate (SC), oil dispersion (OD), or in form of microcapsules.

9. The composition according to claim 1, wherein the total amount of component (i) is equal to or less than 450 g/L, based on the total amount of the composition.

10. The composition according to claim 1, wherein the total amount of component (i) is equal to or less than 300 g/L, based on the total amount of the composition.

11. The composition according to claim 1, wherein the total amount of component (ii) is in the range of from 3 to 6 g/L, based on the total amount of the composition.

12. The composition according to claim 1, wherein
the total amount of component (i) is in the range of from 125 to 250 g/L,
and
the total amount of component (ii) is in the range of from 3 to 6 g/L,
in each case based on the total amount of the composition.

13. A method for producing the herbicidal composition as defined in claim 1, comprising
(a) providing component (i),
(b) providing component (ii), and
(c) combining component (i) and component (ii),
such that the herbicidal composition as defined in claim 1 is obtained.

14. A method for
controlling undesired plant growth,
and/or
controlling harmful plants,
comprising applying a composition comprising (i) glufosinate and/or an agronomically acceptable salt thereof, and ii) indaziflam onto the undesired plant growth or the harmful plants, on parts of the undesired plant growth or the harmful plants, or on the area where the undesired plant growth or the harmful plants grow; wherein the ratio by weight of the total amount of (i) to the total amount of (ii) is in a range of from 25:1 to 50:1 based on the total amount of the composition; wherein (i) and (ii) are the only agriculturally actives applied; and wherein (i) and (ii) together provide better herbicidal activity than (i) or (ii) alone.

15. The method according to claim 14, wherein the total amount per hectare per Gregorian calendar year of component (i) glufosinate and/or the agronomically acceptable salt thereof does not exceed 1500 g.

16. The method according to claim 14, wherein the total amount per hectare per Gregorian calendar year of component (ii) indaziflam does not exceed 30 g.

17. The method according to claim 14, wherein the total amount per hectare per Gregorian calendar year of component (i) glufosinate and/or the agronomically acceptable salt thereof does not exceed 1250 g.

18. The method according to claim 14, wherein the total amount per hectare per Gregorian calendar year of component (ii) indaziflam does not exceed 25 g.

* * * * *